United States Patent
Mitani (10) Patent No.: US 7,534,987 B2
(45) Date of Patent: May 19, 2009

(54) LIGHT MEASURING APPARATUS

(75) Inventor: Yoshiyuki Mitani, Hachioji (JP)

(73) Assignee: Olympus Corporation, Tokyo (JP)

( * ) Notice: Subject to any disclaimer, the term of this patent is extended or adjusted under 35 U.S.C. 154(b) by 61 days.

(21) Appl. No.: 11/904,710

(22) Filed: Sep. 28, 2007

(65) Prior Publication Data
US 2008/0258041 A1   Oct. 23, 2008

Related U.S. Application Data

(63) Continuation of application No. PCT/JP2006/306935, filed on Mar. 31, 2006.

(30) Foreign Application Priority Data

Apr. 1, 2005  (JP)  ............................. 2005-106530

(51) Int. Cl.
*H01J 40/14* (2006.01)
*G01J 1/32* (2006.01)
(52) U.S. Cl. ...................... 250/216; 250/205; 250/239; 359/385
(58) Field of Classification Search ... 250/201.1–201.4, 250/205, 216, 239; 359/384, 385, 391, 738
See application file for complete search history.

(56) References Cited

U.S. PATENT DOCUMENTS 5,612,818 A * 3/1997 Kumagai et al. ............ 359/385

2007/0081241 A1 * 4/2007 Hayashi ...................... 359/443

FOREIGN PATENT DOCUMENTS

| JP | 7-92392 | 4/1995 |
|---|---|---|
| JP | 7-244238 | 9/1995 |
| JP | 8-21956 | 1/1996 |
| JP | 11-202212 | 7/1999 |
| JP | 2002-168784 | 6/2002 |
| JP | 2004-245979 | 9/2004 |
| JP | 2004-354347 | 12/2004 |

* cited by examiner

*Primary Examiner*—Kevin Pyo
(74) *Attorney, Agent, or Firm*—Scully, Scott, Murphy & Presser, P.C.

(57) ABSTRACT

A light measuring apparatus includes a light source configured to emit light to a sample, and a light guide optics system configured to guide light generated as a result of applying the emitted light to the sample, to a photodetector, wherein the light guide optics system is provided in a lightproof unit, and includes optical elements for guiding the generated light to the photodetector, a positioning part for adjusting a position of at least one of the optical elements, and a position detecting part for detecting a position of at least one of the optical elements by an optical method, and the light measuring apparatus comprises a position adjusting part which adjusts the positions of the optical elements by controlling the positioning part and position detecting part, and a light emission control unit which controls operations of starting and stopping light emission of the position detecting part.

7 Claims, 6 Drawing Sheets

| | Light position detector on | Light position detector off |
|---|---|---|
| Count rate [kHz] | 5~6 | 0.2~0.5 |

FIG. 9

LIGHT MEASURING APPARATUS

CROSS-REFERENCE TO RELATED APPLICATIONS

This is a Continuation application of PCT application No. PCT/JP2006/306935, filed Mar. 31, 2006, which was published under PCT Article 21(2) in Japanese.

This application is based upon and claims the benefit of priority from prior Japanese Patent Application No. 2005-106530, filed Apr. 1, 2005, the entire contents of which are incorporated herein by reference.

BACKGROUND OF THE INVENTION

1. Field of the Invention

The present invention relates to a light measuring apparatus capable of obtaining measurement data with a high signal-to-noise ratio by effectively decreasing noise light.

2. Description of the Related Art

A 1-molecule fluorometric analyzer using a confocal optical system needs a complex optical system. A complex optical system mentioned here is configured to be able to adjust an optical path in a confocal optical system, and to change combination of complex filters corresponding to various wavelengths.

Jpn. Pat. Appln. KOKAI Publication No. 7-244238 discloses a confocal scanning microscope, which does not require adjusting an optical path. In this invention, a wavelength of light from one set of variable wavelength laser light source is changed by using a wavelength select reflector, and it is unnecessary to change two or more laser light sources, and an optical path is free from displacement.

Bioluminescence and fluorescent light emitted from a living sample are generally very weak in most cases. A measuring apparatus based on a confocal optical microscope for measuring such a very weak light uses a highly sensitive photodetector, such as a photoelectric multiplier and avalanche photodiode (APD).

In the invention disclosed by the Jpn. Pat. Appln. KOKAI Publication No. 7-244238, laser beams other than one of a necessary wavelength is cut off, causing loss in the light intensity, and the output is decreased. If the intensity of exciting laser beam is very weak, the intensity of fluorescence emitted from a sample becomes very weak. Thus, it is necessary to increase the photodetector sensitivity, but noise light is also amplified together with signal light.

Noise light includes light generated inside a measuring apparatus, in addition to disturbance light. For example, in a light measuring apparatus which measures a very weak light emitted from a living sample at a single molecule level in solution by using more than one light source, it is necessary to incorporate optical elements in a measuring optical path, such as a pinhole and a filter, to reduce light to a very small area and to detect light with high sensitivity, and it is necessary to adjust the positions of these optical elements with high accuracy.

Generally, the adjustment of the positions of these optical elements is automatically performed by detecting the coordinates of the positions by using a light position detector provided in each optical element. When detecting a very weak light from a sample by using a highly sensitive photodetector, a light beam emitted from a light source that is incorporated inside the light position detector is also detected by the photodetector used for measurement, and this may affect measured data as noise.

BRIEF SUMMARY OF THE INVENTION

A light measuring apparatus according to a first aspect of the present invention comprising: a light source configured to emit light to a sample; and a light guide optics system configured to guide light generated as a result of applying the emitted light to the sample, to a photodetector, wherein the light guide optics system is provided in a lightproof unit to interrupt disturbance light, and includes optical elements for guiding the generated light to the photodetector; a positioning part for adjusting a position of at least one of the optical elements; and a position detecting part for detecting a position of at least one of the optical elements by an optical method, and the light measuring apparatus comprises a position adjusting part which adjusts the positions of the optical elements by controlling the positioning part and position detecting part; and a light emission control unit which controls operations of starting light emission of the position detecting part when adjusting a position of at least one of the optical elements, and stopping light emission of the position detecting part when measuring the sample.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiment 1

Figure 1:
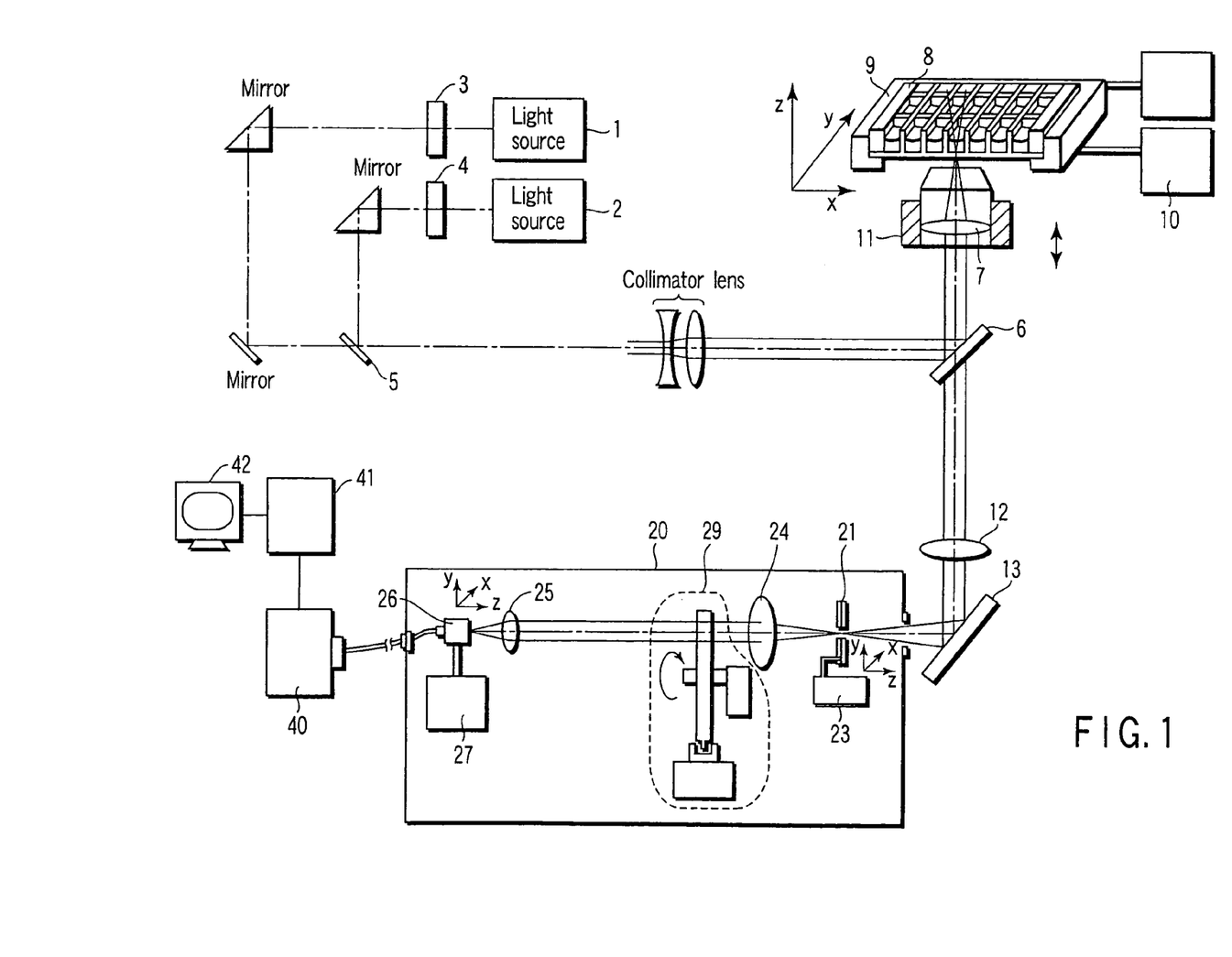
FIG. 1 is a schematic diagram of the configuration of a light measuring apparatus according to a first embodiment of the invention.

FIG. 1 is a schematic diagram of the configuration of a light measuring apparatus according to a first embodiment of the invention. The basic configuration of the main part of the light measuring apparatus according to this embodiment is based on a confocal optical microscope. The configuration and operation of the light measuring apparatus will be explained hereinafter by referring to FIG. 1.

Two kinds of light source are provided in the light measuring apparatus. A light source 1 uses a helium neon laser with an output power of 2 mW and a wavelength of 633 nm. A light source 2 uses an argon laser with an output power of 10 mW and a wavelength of 488 nm.

Light emitted from the light sources 1 and 2 through shutters 3 and 4 is changed in the advancing direction by a mirror, synthesized by a dichroic mirror 5, and made to travel on one optical path. The synthesized one light beam becomes a parallel light beam with an enlarged diameter after passing through a collimator lens, and being reflected by a dichroic mirror 6, and made to arrive at an objective lens 7.

Above the objective lens 7, a micro-plate 8 is mounted on and fixed to a sample stage 9. Horizontal and vertical positions of the micro-plate 8 are adjusted by a sample stage X/Y-axis driving mechanism 10 and an objective lens Z-axis adjusting mechanism 11, so that an area where light is condensed by the objective lens 7, that is, a confocal area is formed within a predetermined area in a well of the micro-plate 8.

The micro-plate 8 used here is made of resin or glass, and has 96 wells. A well mentioned here means a circular or square groove to contain a sample. The bottom of each well is a window formed by material, such as glass to pass visible light (not shown).

The objective lens 7 used here is a 40× magnification immersed objective lens with NA=0.9, for example. Therefore, water is filled between the bottom of the micro-plate 8 and the distal end of the objective lens 7.

A laser beam condensed by the objective lens 7 excites a fluorescent molecule to float within a sample, and fluorescence is emitted from a fluorescent molecule. Rhodamine Green (RhG) is used as a fluorescent substance. Rhodamine Green is most effectively excited near a wavelength of 490 nm of excited light, and most effectively lit near a wavelength of 530 nm. Therefore, sample is excited by an argon laser. Further, Rhodamine Green is excited by a helium neon laser, by using cye-five (Cy5). Cye-five (Cy5) is most effectively excited near a wavelength of 640 nm of excited light, and has highest light-emission intensity near a wavelength of 670 nm.

The fluorescence enters again the objective lens 7, and then enters the dichroic mirror 6. The dichroic mirror 6 used here is formed by coating a multilayer film on one side of a flat glass plate, to have optimum transmission and reflection spectral characteristics. Therefore, the fluorescence transmits through the dichroic mirror 6, reaches a condenser lens 12, reflects on a mirror 13 as a convergent beam, and enters a lightproof box 20.

Figure 2:
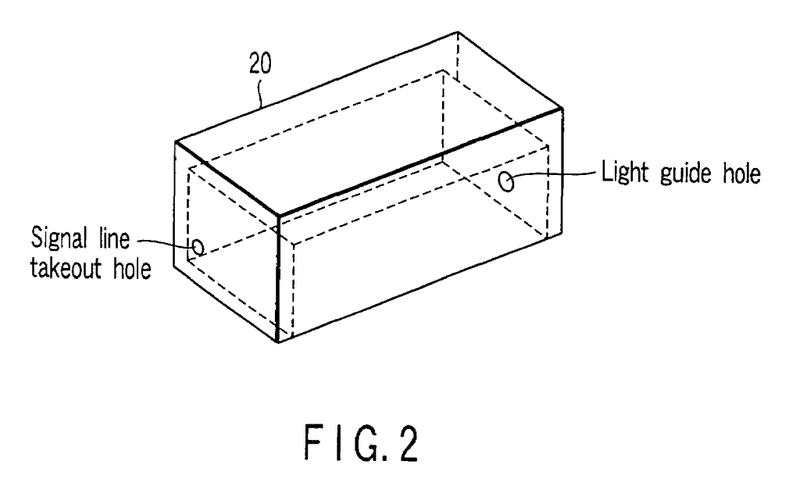
FIG. 2 is a view of a lightproof box.

The lightproof box 20 is a hollow box as shown in FIG. 2, made of metal such as stainless steel or aluminum, provided with a light guide hole and a signal line takeout hole on a sidewall, and placed just like putting over the apparatus. The lightproof box contains a pinhole 21, a collimator lens 24 and a photodetector 26.

The pinhole 21 is arranged at the focal position of the condenser lens 12 in the lightproof box 20. The pinhole 21 is provided with a light position detector (not shown) and a pinhole driver 23. The position of the pinhole 21 can be adjusted in the X/Y/Z-axis direction by the pinhole driver 23. An origin point is obtained based on the values detected by the light position detector. By operating the pinhole driver 23 by a predetermined distance from the origin point, the focal plane of the condenser lens 12 can be almost matched with the aperture plane of the pinhole 21. This is rough adjustment of the pinhole position. The pinhole 21 eliminates a background light generated from the outside of a confocal area of light formed in a well. Further, disturbance light from the outside of the apparatus can be eliminated by providing the lightproof box 20.

Signal light passed through the pinhole 21 is changed to a parallel light by the collimator lens 24. The signal light reaches a lens 25, and condensed on the light-receiving surface of the photodetector 26 by the lens 25. The photodetector 26 is provided with a light position detector (not shown) and a photodetector driver 27. The position of the light-receiving surface of the photodetector can be adjusted along the X/Y/Z-axis direction by the photodetector driver 27. By operating the photodetector driver 27 based on the detected signal of the light position detector, the photodetector 26 can be set to a substantially optimum position. The above is rough adjustment of light detection.

A barrier filter switching mechanism 29 is provided between the collimator lens 24 and lens 25. The barrier filter switching mechanism 29 has barrier filters to transmit light with a desired wavelength from an incident signal light. The barrier filter switching mechanism 29 is rotated to switch and set barrier filters in an optical path.

Figure 3:
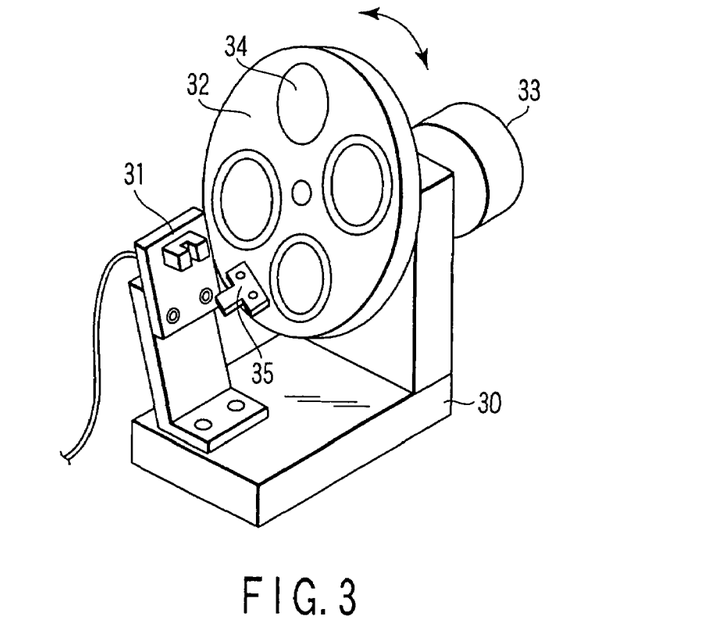
FIG. 3 is a view showing the configuration of a barrier filer switching mechanism.

FIG. 3 is a view showing the configuration of the barrier filer switching mechanism 29.

The barrier filter switching mechanism 29 consists of a light position detector 31 provided on a base 30, a barrier filter rotary switch 32, and a barrier filter rotary switch driver 33.

The barrier filter rotary switch 32 is shaped like a circular plate as shown in FIG. 3, and its center axis is connected to the barrier filter rotary switch driver 33. Therefore, by driving the barrier filter rotary switch driver 33, the barrier filter rotary switch can be rotated about the center of the circular plate as an axis of rotation.

The center of the barrier filter 34 coincides with a position separated by a predetermined distance from the center of rotation of the barrier filter rotary switch 32. Namely, the barrier filters 34 are arranged by aligning the center with the circumference of the concentric circle of the barrier filter rotary switch 32. Therefore, by driving the barrier filter rotary switch driver 33, a necessary barrier filter 34 can be placed in an optical path paralleled by the collimator lens 24. The barrier filter 34 can be securely placed in the optical path.

The barrier filter 34 is adjusted in a transmitted light spectrum to meet the intensity distribution of fluorescence emission spectrum, and transmits only light with a wavelength range of emission spectrum of fluorescence as signal light. Wavelengths of fluorescence and background light are different. Therefore, a scattered light generated in a predetermined well of the micro-plate 8 can be cut off. It is also possible to cut off noise light generated when a part of an incident light reflects on a wall of a well and returns to an incident optical path.

A position detecting target 35 is provided at a predetermined position of the barrier filter rotary switch 32. The position detecting target 35 is rotated together with the rotation of the barrier filter rotary switch 32.

Figure 4A:
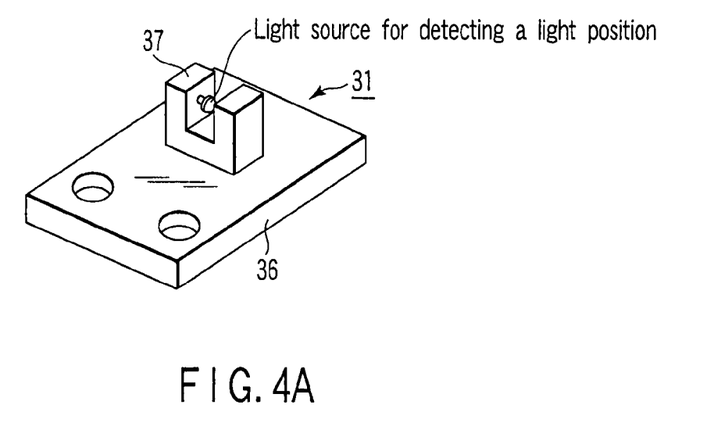
FIG. 4A is a view of a light position detector.
Figure 4B:
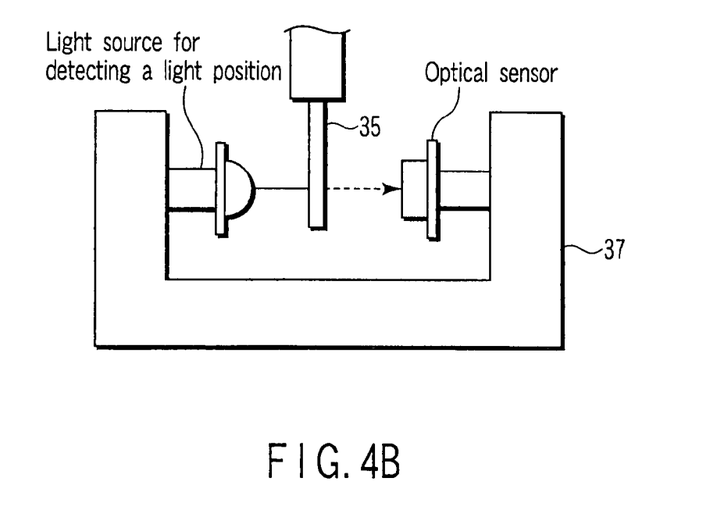
FIG. 4B is a view of a light position detector.

FIGS. 4A and 4B show the light position detector 31.

FIG. 4A is a perspective view of the light position detector 31. The light position detector 31 has a structure that a U-shaped detector 37 is provided on a fixing member 36 connected to the base 30. A light source for detection is provided in one side of the detector 37, and an optical sensor is provided on the other side.

FIG. 4B is an enlarged side view of the detector 37. The position detecting light source and optical sensor are held face to face, and the position detecting target 35 passes between them. Therefore, when the position detecting target 35 is located between the optical sensor and the light source of position detecting detector 31, the light from the light source is blocked and the optical sensor does not output. The output of the optical sensor is 5V when the position detecting target 35 does not exist, and 0V when the position detecting target 35 exists in front of the optical sensor, for example. By observing changes of the optical sensor output, an origin point of a rotating position of the barrier filter rotary switch 32 can be detected. Namely, by counting the rotating drive pulses of the barrier filter rotary switch driver 33 by taking a position where the optical sensor output becomes 0V as an origin point, the rotating position of the barrier filter rotary switch 32 can be known.

A light source of the light position detector 31 may be an infrared LED, or a semiconductor laser. The optical sensor may be a semiconductor optical sensor.

In FIG. 1, the photodetector 26 is an avalanche photodiode (APD), or a weak photodetector such as a photoelectric multiplier. Signal light received by the photodetector 26 is an extremely weak light, and a photon pulse. The photodetector 26 converts signal light to a photoelectric pulse as an electrical signal. The converted photoelectric pulse is applied to a signal processor 40, and amplified there. Then, the photoelectric pulse is waveform shaped, converted to an on-off voltage pulse, and guided to a computer 41.

The voltage pulse is stored in a memory (not shown) of the computer 41, and operations such as correlative analysis will be performed. As a result, analysis results, such as the life as well as the intensity of fluorescence, an auto-correlation function of intensity fluctuation, or cross-correlation function are displayed in a display 42 of the computer 41.

The light position detector 31 adopts the above-mentioned light detection system. Because, comparing with a contact type position detector or a detector utilizing electrostatic capacitance, a semiconductor light position detector is low cost, compact, and easy to handle. However, when using a light position detector for adjusting the positions of optical elements, light emitted from a light source used by a light position detector becomes noise light for a photodetector used for measurement. Therefore, it is necessary to take a measure of decreasing or interrupting noise light for correct detection of a light signal.

Next, explanation will be given on the measuring operation of a light measuring apparatus, including the corrective measures for noise light, with reference to FIGS. 5 to 8.

Figure 5:
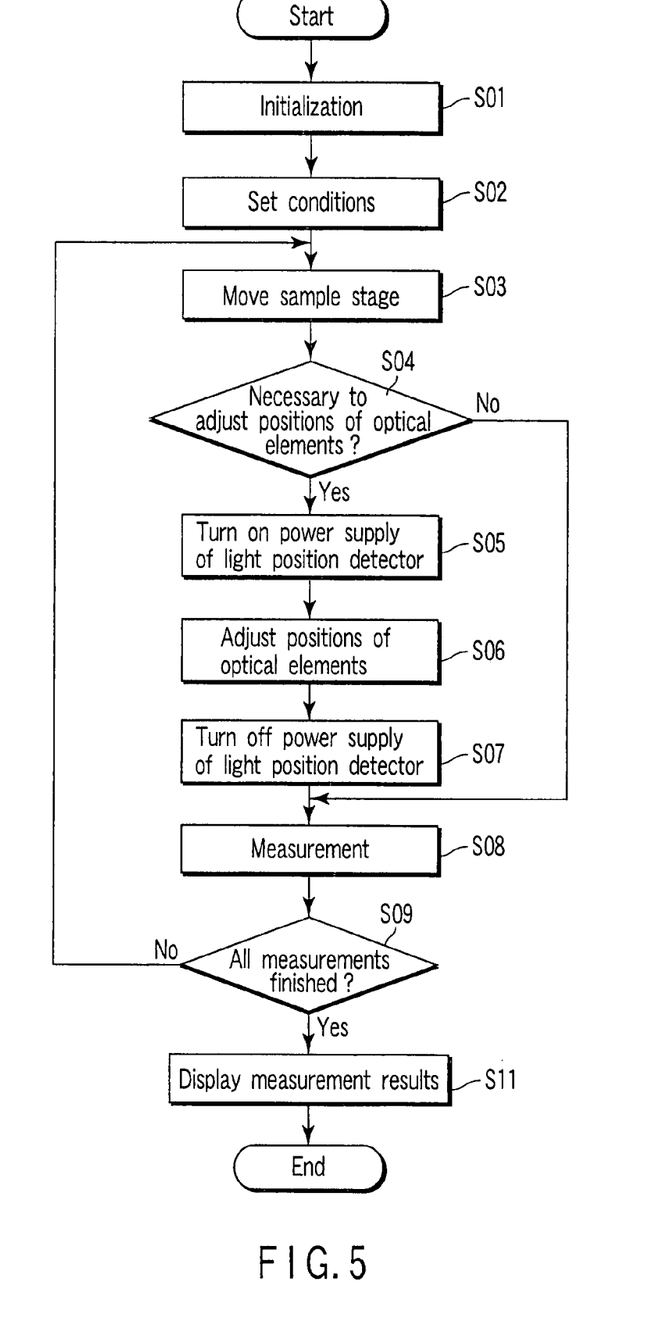
FIG. 5 is a flowchart showing a procedure of automatic measurement by a computer.

FIG. 5 is a flowchart showing a procedure of automatic measurement by the computer 41.

In step S01, when the user turns on a main power supply of a light measuring apparatus, the computer 41 starts initialization. Namely, the computer adjusts the positions of optical elements and movable parts such as a sample stage to initial positions. The initial position means the position where the optical element is driven by a predetermined step count from an origin point.

For example, when adjusting the barrier filter rotary switch 32 to its initial position, perform as follows. First, rotate the position detecting target 35, and assumes the position where the light position detector 31 detects the position detecting target 35, to be an origin point. Rotate the barrier filter rotary switch 32 by a predetermined angle from this origin point, and assume that position to be an initial position. Likewise, for the initial positions of the pinhole 21 and photodetector 26, monitor output signals of a light position detector (not shown), and set the initial positions based on the output values and predetermined number of rotary drive pulses.

In step S02, obtain measuring conditions, such as measuring time, specification of a light source used for measurement, and specification of wells as objects of measurement. These measuring conditions are directly input by the user.

In step S03, drive the sample stage X/Y-axis driving mechanism 10 and determine the horizontal position of the sample stage 9, so that a well to be measured is placed right above the objective lens 7.

In step S04, check whether it is necessary to adjust the positions of optical elements. For example, when measuring for the first time, when measuring wells more than a predetermined number, or when measuring a well in a specific area of the microscope 8, check whether the positions meet the readjustment conditions.

When Yes in the step S04, turn on the power supply of the light position detector in steps S05-S06, and determines the positions of optical elements. First, open the shutters 3 and 4 for the light sources 1 and 2, and apply light to a sample solution in a well through the objective lens 7. While detecting a fluorescent signal emitted from the sample by the photodetector 26 for measurement, adjust the positions of the optical elements in the optical path where the signal light passes, in the optical axis direction and in the X/Y-axis direction (horizontal direction), and optimize the setting positions of the optical elements. In this time, use a light position detector for adjusting the positions of the optical elements.

For the positions of the pinhole 20 and photodetector 26, for example, make rough adjustment by driving the pinhole driver 23 and photodetector driver 27, according to an original position obtained from the output value of the light position detector (not shown) and a predetermined number of rotation drive pulses. Then, open the shutter, and determine the optimum positions by making fine adjustment of the positions of the pinhole driver 23 and photodetector driver 27, so that the output of the photodetector 26 becomes the largest as described above.

After the positions of all optical elements are adjusted, it becomes unnecessary to use a light position detector. If the power supply of the light position detector is left on, the light emitted from the light source used in the light position detector is detected as noise by the photodetector 26. Therefore, in step S07, after the positions of all optical elements are adjusted and the optical axis of the measuring apparatus is adjusted, the computer 41 turns off the power supply of the light position detector and stops generation of noise light. Disturbance light is cut off by the lightproof box 20, and an optical noise generated in the lightproof box is cut off by turning off the power supply of the light position detector. Therefore, noise light other than a measuring signal is eliminated.

When measurement is finished in step S08, the user checks whether all specified wells have been measured in step S09. If any well is left not yet measured, repeat the operations of steps S03 to S09.

Namely, drive the sample stage 9, move the horizontal position of the micro-plate 8, and position a sample in a well of the micro-plate 8 to be measured next. In this time, if the positions of optical elements need to be adjusted in step S04, turn on the power supply of the light position detector, and re-adjust the positions. After the positions are adjusted, turn off the power supply of the light position detector.

When all wells specified by the user are measured in step S09, the measured data is displayed in the display 42 in step S11.

Figure 6:
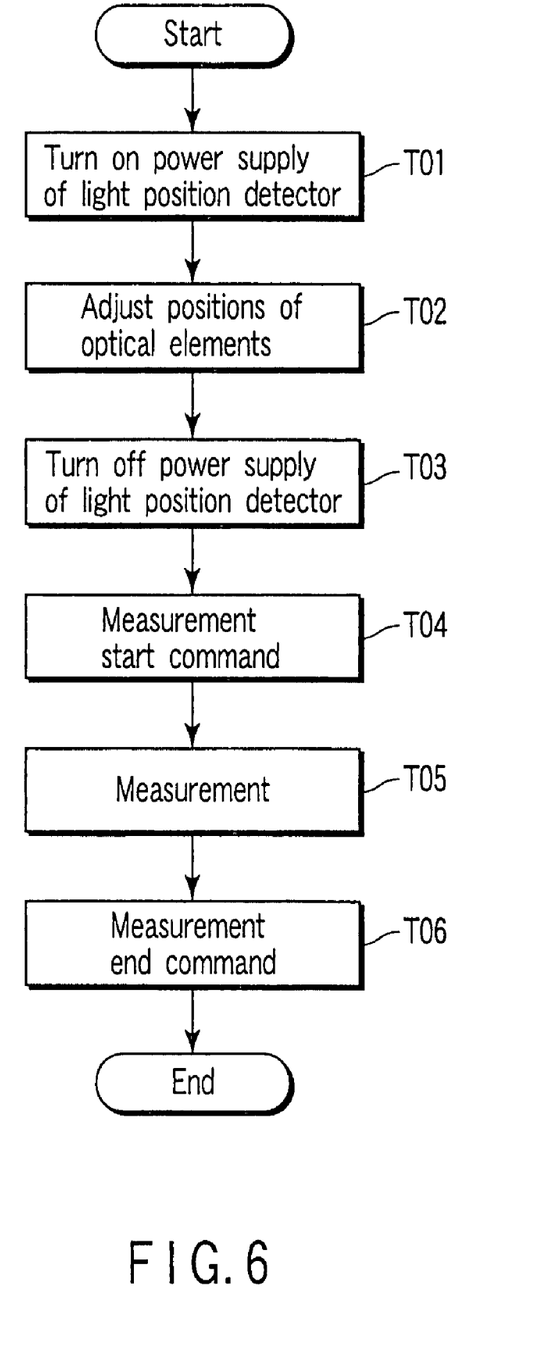
FIG. 6 is a flowchart showing a procedure of automatic operation of a computer.

FIG. 6 is a flowchart showing an automatic operation procedure of the computer 41 corresponding to the operations of steps S05-S08 in FIG. 5.

In steps T01-T03, the computer 41 turns on the power supply of the light position detector, and adjusts the positions of necessary optical elements. Then, the computer turns off the power supply of the light position detector. In step T04, the computer outputs a measurement start command. Receiving the measurement start command, each part of the light measuring apparatus executes a series of operations to start predetermined measurement. For example, the shutters 3 and 4 are opened. When measurement is finished, the computer 41 outputs a measurement end command in step T06. Receiving the measurement end command, each part of the light measuring apparatus executes a series of operations to finish measurement. For example, the shutters 3 and 4 are closed.

According to the first embodiment, the optical elements requiring position adjustment are surrounded by the lightproof box 20, which prevents disturbance light in the apparatus. By combining the emission adjustment of the abovementioned light position and the light-proof box 20, both of disturbance light and stray light from the light position detector can be cut off. Therefore, noise light during measurement can be largely decreased.

Modification 1 of Embodiment 1

In the modification 1 of the first embodiment, the power supply of the light position detector is turned off during measurement and turned on after measurement. This is the same as in the first embodiment. The difference is to use a logic circuit of the light measuring apparatus for judgment.

Figure 7:
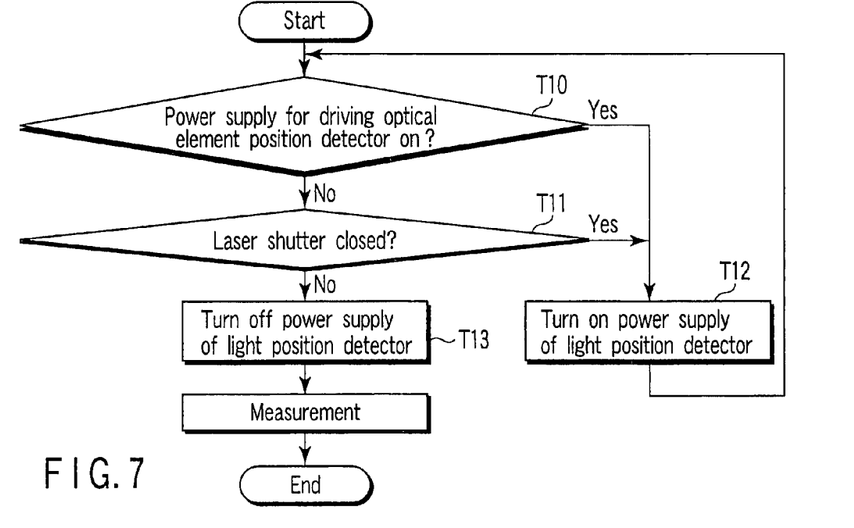
FIG. 7 is a flowchart showing the logic of turning on or off a power supply of a light position detector.

FIG. 7 is a flowchart showing the logic of turning on or off the power supply of the light position detector. When an optical element position driving power supply that supplies power to a motor for adjusting positions of optical elements is operating as shown in step T10, or when a shutter of a laser light source is closed as shown in step T11, it is judged that measurement is not performed. The power supply of the light position detector is turned on in step T12. Contrarily, when these two conditions are not established, it is judged to be during measurement, and the power supply of the light position detector is turned off.

In the modification 1, when the shutter of laser used as a light source is opened and a driving source for switching all optical elements is not operating, that is, when optical adjustment is finished and measurement is ready to execute, a control of turning off the power supply of the light position detector is performed electrically, or on an electrical circuit. Therefore, it can be prevented that an infrared ray as light emitted from the light position detector during measurement is detected as stray light by the photodetector.

Modification 2 of Embodiment 1

In the modification 2 of the first embodiment, the power supply of the light position detector is turned off during measurement and turned off after measurement. The difference is that a switch to turn on or off the power supply of the light position detector is provided in the main body of the light measuring apparatus, and the operator manually turns on the power supply of the light position detector when adjusting the optics and turns off the power supply of the light position detector when measuring light.

Figure 8:
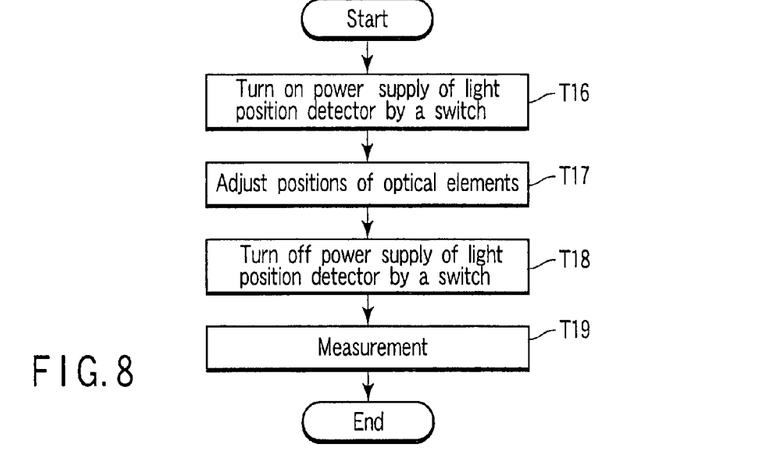
FIG. 8 is a flowchart showing an automatic operation of a computer according to a modification of the invention.

FIG. 8 a flowchart showing a procedure concerning the modification 2 corresponding to the operations of steps S05 to S08 in FIG. 5.

In step T16, the operator turns on the power supply of the light position detector by operating a switch, and instructs the computer 41 to start adjustment of the positions of optical elements. Receiving the instruction, the computer 41 adjusts the positions of necessary optical elements in step T17. The computer displays a position adjustment end message in the display 42. The operator confirms this message, and turns off the power supply of the light position detector by operating a switch in step T18, and instructs the computer to start measurement.

In step T19, the computer 41 starts a series of measuring operations. Namely, the computer outputs a measurement start command. Each part of the light measuring apparatus receives this measurement start command, and executes a predetermined series of measurement starting operations. For example, the shutters 3 and 4 are opened. When the measurement is finished, the computer 41 outputs a measurement end command. Each part of the light measuring apparatus receives this measurement end command, and executes a predetermined series of measurement ending operations.

In the modification 2, in addition to electric automatic control as a method of preventing stray light, it is also possible to obtain the similar effect by manually turning off the power supply of the light position detector at the end of optical adjustment. Therefore, it is possible to realize a desired effect, that is, decreasing noise light, by a simply configured apparatus.

RESULTS OF APPLICATION TO ACTUAL APPARATUS

By using the light measuring apparatus configured as explained above, set the micro-plate 8 on the sample stage 9 and fill a phosphate buffer solution (PBS) as a buffer liquid in a well, after adjusting the optical axis. Emit a helium neon laser beam of 300 µW with a wavelength of 633 nm to the well. Measure the value of the output from the photodetector 26, or the count rate, obtained in this time. Fluorescent substance is not contained in the phosphate buffer solution used as a buffer liquid.

Compare the output values obtained when the power supply of the light position detector is turned on and off. The measurement time is 10 seconds.

Figure 9:
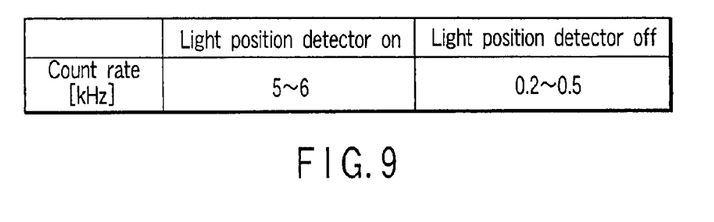
FIG. 9 is a table of measurement results.

FIG. 9 shows the measurement results. The count rate of the optical pulse signal output from the photodetector 26 is 0.2-0.5 kHz, even if an excited light is emitted to the solution containing a sample not including a fluorescent substance. The output signal obtained in that time is considered a dark current. When the power supply of the light position detector is turned on, the optical pulse signal output from the photodetector 26 is 5-6 kHz.

According to the results shown in FIG. 9, it is seen that the light source of the position detector necessary for optical adjustment causes large internal noise light. It is also seen that the influence of this noise light can be effectively decreased by turning on or off the light position detector according to the present invention.

Light handled by this light measuring apparatus is not limited to a laser beam. A tungsten lamp may be used as a light source. Light to be detected is not limited to fluorescence, but may be phosphorescence, emitted light, scattered light and reflected light.

Effects of the Embodiment

The embodiment enables arrangement of complex optics using two or more light sources for position adjustment by detecting positions and angles of optical elements by a light position detector. The embodiment can cut off noise light generated then, and provides accurate measurement.

By combining a power supply control of a light position detector and a lightproof box, the embodiment can cut off both disturbance light and noise light in the apparatus, thereby providing measurement data with a high signal-to-noise ratio.

By using a light position detector when adjusting optical elements and turning off the power supply when measuring a sample, the embodiment can perform both correct optical axis adjustment and highly sensitive measurement.

The present invention is not limited to the above-described embodiments, but may be embodied in other forms by modifying the components without departing from its essential characteristics. The invention may be embodied in various forms by combining the components disclosed in the above-described embodiments. For example, some components may be deleted from all components shown in the embodiments. Components of different embodiments may be combined.

What is claimed is:

1. A light measuring apparatus comprising:

a light source configured to emit light to a sample; and a light guide optics system configured to guide light generated as a result of applying the emitted light to the sample, to a photodetector, wherein the light guide optics system is provided in a lightproof unit to interrupt disturbance light, and includes optical elements for guiding the generated light to the photodetector;

a positioning part for adjusting a position of at least one of the optical elements; and a position detecting part for detecting a position of at least one of the optical elements by an optical method, and the light measuring apparatus comprises a position adjusting part which adjusts the positions of the optical elements by controlling the positioning part and position detecting part; and a light emission control unit which controls operations of starting light emission of the position detecting part when adjusting a position of at least one of the optical elements, and stopping light emission of the position detecting part when measuring the sample.

2. The light measuring apparatus according to claim 1, wherein the position adjusting part starts operation of adjusting the positions of the optical elements when predetermined conditions are established; and the predetermined conditions include at least one of first measurement after power is turned on, measurement more than a predetermined number, and measurement of a sample at a specific position.

3. The light measuring apparatus according to claim 2, wherein the optical elements include at least a pinhole and a filter having a function of selectively transmitting or reflecting a wavelength of an incident light.

4. The light measuring apparatus according to claim 3, wherein the light emission control unit starts light emission of the position detecting part when at least one of two conditions, that is, an optical shutter to emit light to the sample is closed, and a driving power supply of a positioning means of at least one of the optical elements are operating, is established, and stops light emission of the position detecting part when neither of the two conditions is established.

5. The light measuring apparatus according to claim 1, wherein the optical elements include at least a pinhole and a filter having a function of selectively transmitting or reflecting a wavelength of an incident light.

6. The light measuring apparatus according to claim 5, wherein the light emission control unit starts light emission of the position detecting part when at least one of two conditions, that is, an optical shutter to emit light to the sample is closed, and a driving power supply of a positioning means of at least one of the optical elements are operating, is established, and stops light emission of the position detecting part when neither of the two conditions is established.

7. The light measuring apparatus according to claim 1, wherein the light emission control unit starts light emission of the position detecting part when at least one of two conditions, that is, an optical shutter to emit light to the sample is closed, and a driving power supply of a positioning means of at least one of the optical elements are operating, is established, and stops light emission of the position detecting part when neither of the two conditions is established.

* * * * *